US010864029B2

(12) United States Patent
Redmond et al.

(10) Patent No.: US 10,864,029 B2
(45) Date of Patent: Dec. 15, 2020

(54) SACROILIAC JOINT STABILIZATION AND FIXATION DEVICES AND RELATED METHODS

(71) Applicant: WEST END BAY PARTNERS, LLC, Tyler, TX (US)

(72) Inventors: Andy J. Redmond, Tyler, TX (US); Charles R. Gordon, Tyler, TX (US); Erik Wagner, Austin, TX (US); Michael E. Landry, Austin, TX (US)

(73) Assignee: WEST END BAY PARTNERS, LLC, Tyler, TX (US)

( * ) Notice: Subject to any disclaimer, the term of this patent is extended or adjusted under 35 U.S.C. 154(b) by 5 days.

(21) Appl. No.: 16/257,789

(22) Filed: Jan. 25, 2019

(65) Prior Publication Data

US 2019/0231405 A1 Aug. 1, 2019

Related U.S. Application Data

(60) Provisional application No. 62/622,649, filed on Jan. 26, 2018.

(51) Int. Cl.
*A61B 17/70* (2006.01)
*A61B 17/84* (2006.01)
(Continued)

(52) U.S. Cl.
CPC ........ *A61B 17/844* (2013.01); *A61B 17/7055* (2013.01); *A61B 17/8625* (2013.01);
(Continued)

(58) Field of Classification Search
CPC ................ A61B 17/70; A61B 17/72; A61B 17/7233–7275; A61B 17/7065;
(Continued)

(56) References Cited

U.S. PATENT DOCUMENTS 5,522,899 A 6/1996 Michelson
5,693,100 A 12/1997 Pisharodi
(Continued)

OTHER PUBLICATIONS

"Sacroiliac (SI) Joint Fusion Technique," *SPINEMarketGroup*, Apr. 19, 2016 [http://www.thespinemarketgroup.com/si-joint-fusion/; Accessed: Apr. 25, 2016].
(Continued)

*Primary Examiner* — Eduardo C Robert
*Assistant Examiner* — Michelle C Eckman
(74) *Attorney, Agent, or Firm* — Norton Rose Fulbright US LLP

(57) ABSTRACT

An anchor device for use in sacroiliac joint stabilization comprises a housing having one or more apertures; one or more engagement members at least partially disposed in the housing, where at least one of the one or more engagement members is movable between a retracted position and an extended position such that, when in the extended position, the at least one of the one or more engagement members extends through at least one of the one or more apertures; wherein, when in the extended position, the at least one of the one or more engagement members is configured to move to the extended position within cancellous bone of a sacrum; and wherein the anchor device comprises a continuous channel extending from a first end of the anchor device to a second end of the anchor device, the channel being configured to receive a guidewire.

19 Claims, 14 Drawing Sheets

(51) Int. Cl.
*A61B 17/86* (2006.01)
*A61B 17/88* (2006.01)
(52) U.S. Cl.
CPC ...... *A61B 17/8685* (2013.01); *A61B 17/8888* (2013.01); *A61B 2017/8655* (2013.01)
(58) Field of Classification Search
CPC ....... A61B 17/84; A61B 17/844; A61B 17/86; A61B 2017/8655; A61F 2/44; A61F 2002/30995
See application file for complete search history.

(56) References Cited

U.S. PATENT DOCUMENTS

| | | | | |
|---|---|---|---|---|
| 6,053,916 | A * | 4/2000 | Moore | A61F 2/30988 606/86 R |
| 6,129,763 | A * | 10/2000 | Chauvin | A61F 2/446 623/17.11 |
| 6,371,987 | B1 * | 4/2002 | Weiland | A61F 2/4455 623/17.11 |
| 7,128,760 | B2 * | 10/2006 | Michelson | A61F 2/446 623/17.15 |
| 7,828,848 | B2 | 11/2010 | Chauvin et al. | |
| 8,187,332 | B2 | 5/2012 | McLuen | |
| 8,551,171 | B2 | 10/2013 | Johnson et al. | |
| 8,562,651 | B2 | 10/2013 | Metcalf et al. | |
| 8,795,335 | B1 * | 8/2014 | Abdou | A61B 17/7065 606/247 |
| 8,900,279 | B2 | 12/2014 | Assell et al. | |
| 8,986,348 | B2 | 3/2015 | Reiley | |
| 9,089,371 | B1 | 7/2015 | Faulhaber | |
| D742,517 | S * | 11/2015 | Schifano | D24/155 |
| 9,492,284 | B2 * | 11/2016 | Ginn | A61B 17/1604 |
| 9,788,961 | B2 * | 10/2017 | Donner | A61F 2/30988 |
| 9,814,598 | B2 * | 11/2017 | Ainsworth | A61F 2/447 |
| 10,172,656 | B1 * | 1/2019 | Reimels | A61B 17/844 |
| 2002/0022887 | A1 | 2/2002 | Huene | |
| 2002/0049447 | A1 * | 4/2002 | Li | A61B 17/68 606/916 |
| 2005/0177158 | A1 * | 8/2005 | Doubler | A61B 17/7225 606/64 |
| 2008/0140082 | A1 * | 6/2008 | Erdem | A61B 17/8805 606/92 |
| 2008/0161822 | A1 * | 7/2008 | Perez-Cruet | A61B 17/7065 606/99 |
| 2008/0208264 | A1 * | 8/2008 | Lazarof | A61C 8/0022 606/310 |
| 2008/0262497 | A1 * | 10/2008 | Nijenbanning | A61B 17/84 606/63 |
| 2009/0099610 | A1 * | 4/2009 | Johnson | A61B 17/7055 606/86 R |
| 2009/0292316 | A1 * | 11/2009 | Hess | A61B 17/7065 606/249 |
| 2010/0057130 | A1 * | 3/2010 | Yue | A61B 17/7065 606/249 |
| 2010/0100135 | A1 * | 4/2010 | Phan | A61B 17/7064 606/301 |
| 2010/0106191 | A1 * | 4/2010 | Yue | A61B 17/7068 606/249 |
| 2010/0152786 | A1 * | 6/2010 | Behrbalk | A61B 17/68 606/301 |
| 2011/0144766 | A1 * | 6/2011 | Kale | A61B 17/686 623/23.63 |
| 2011/0282396 | A1 * | 11/2011 | Shimko | A61C 8/0074 606/303 |
| 2011/0319946 | A1 | 12/2011 | Levy et al. | |
| 2012/0109222 | A1 * | 5/2012 | Goel | A61B 17/8625 606/310 |
| 2012/0191135 | A1 * | 7/2012 | Abdou | A61B 17/7065 606/248 |
| 2012/0191191 | A1 * | 7/2012 | Trieu | A61B 17/8665 623/17.11 |
| 2013/0053902 | A1 * | 2/2013 | Trudeau | A61B 17/844 606/313 |
| 2013/0123857 | A1 * | 5/2013 | Biedermann | A61B 17/744 606/303 |
| 2013/0245703 | A1 | 9/2013 | Warren et al. | |
| 2013/0310883 | A1 * | 11/2013 | Levy | A61B 17/863 606/313 |
| 2014/0371795 | A1 * | 12/2014 | Hess | A61B 17/7065 606/249 |
| 2015/0012051 | A1 | 1/2015 | Warren et al. | |
| 2015/0080972 | A1 * | 3/2015 | Chin | A61B 17/863 606/304 |
| 2015/0147722 | A1 * | 5/2015 | Tsai | A61B 17/72 433/174 |
| 2015/0201979 | A1 * | 7/2015 | Paul | A61B 17/7225 606/62 |
| 2015/0313720 | A1 | 11/2015 | Lorio | |
| 2016/0262805 | A1 * | 9/2016 | Rogers | A61B 17/7065 |
| 2017/0156766 | A1 * | 6/2017 | Anderson | A61F 2/30771 |
| 2017/0258498 | A1 * | 9/2017 | Redmond | A61B 17/8685 |
| 2017/0340370 | A1 * | 11/2017 | Chen | A61B 17/7225 |
| 2019/0231405 | A1 * | 8/2019 | Redmond | A61B 17/8685 |
| 2020/0038070 | A1 * | 2/2020 | Suddaby | A61B 17/1671 |
| 2020/0046413 | A1 * | 2/2020 | Thornes | A61B 17/863 |
| 2020/0113605 | A1 * | 4/2020 | Redmond | A61B 17/7055 |

OTHER PUBLICATIONS

"Silex Sacroiliac Joint Fusion System," *X-Spine Product Guide*, Miamisburg, OH: 2013.
"Silex: Sacroiliac Joint Fusion System," *X-Spine*, [http://x-spine.com/surgeons/sacroiliac-joint/silex/; Accessed Oct. 8, 2015].
"Zyga SImmetry Patient Animation" [https://www.youtube.com/watch?v=ynQE5kIU98c; Accessed Aug. 4, 2017].
Faruqi, Omar, "Life Spine Announces Limited Release Simpact Sacroiliac Joint Fixation System," Press Release. Huntley, IL, Oct. 6, 2015.
Globus Medical SI-LOK Sacroiliac Joint Fixation System [http://si-lok.globusmedical.com/; Accessed Aug. 4, 2017].
LifeSpine SImpact Sacroiliac Joint Fixation System [https://lifespine.com/simpact/; Accessed Aug. 4, 2017].
Linhardt, Matt. "CoreLink Releases the Entasis SI Joint Fusion System" *BusinessWire*, St. May 3, 2016.
SI-Bone iFuse Implant System [https://si-bone.com/patients/ifuse-implant-system/; Accessed Aug. 4, 2017].
Substantial Equivalence Determination issued by the Food and Drug Administration for , 510(k) No. K152237, "The Entasis Dual-Lead Sacroiliac Implant," issued Feb. 4, 2016.
Twork et al., "Fixating on Innovation: A Revolution in Spinal Fusion Surgery," *Medical Design Briefs*, Mar. 2017.
Zimmer TriCor Sacroiliac Joint Fusion System [http://www.zimmer.com/medical-professionals/products/spine/tricor-sacroiliac-joint-fusion-system.html; Accessed Aug. 4, 2017].

* cited by examiner

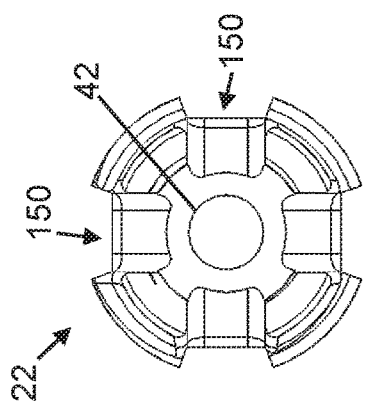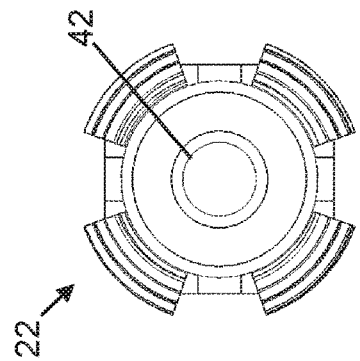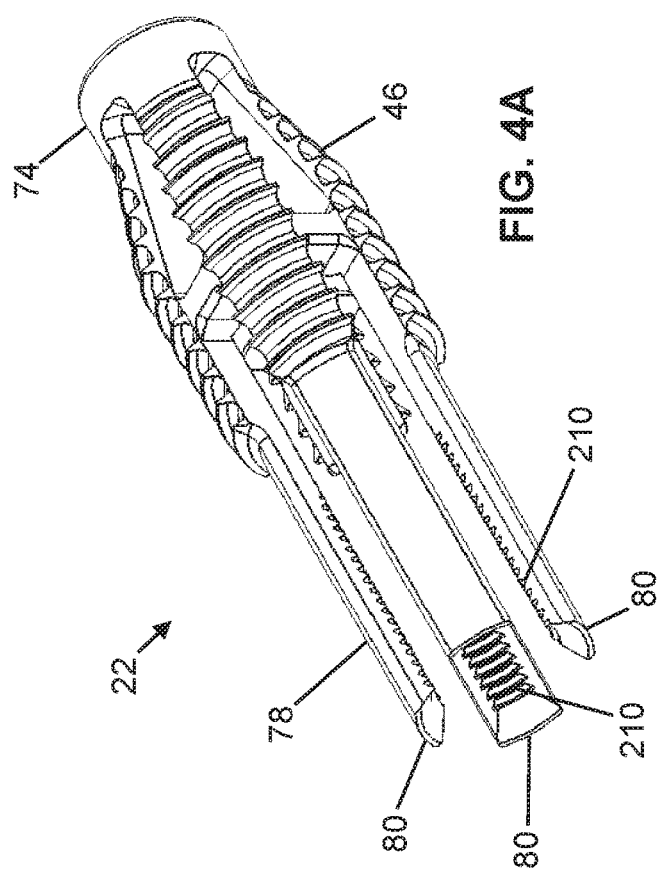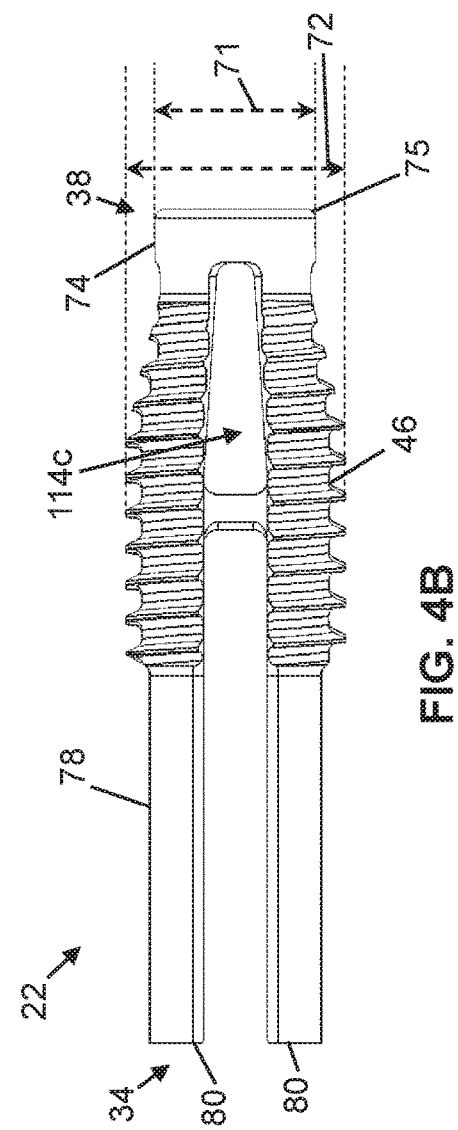

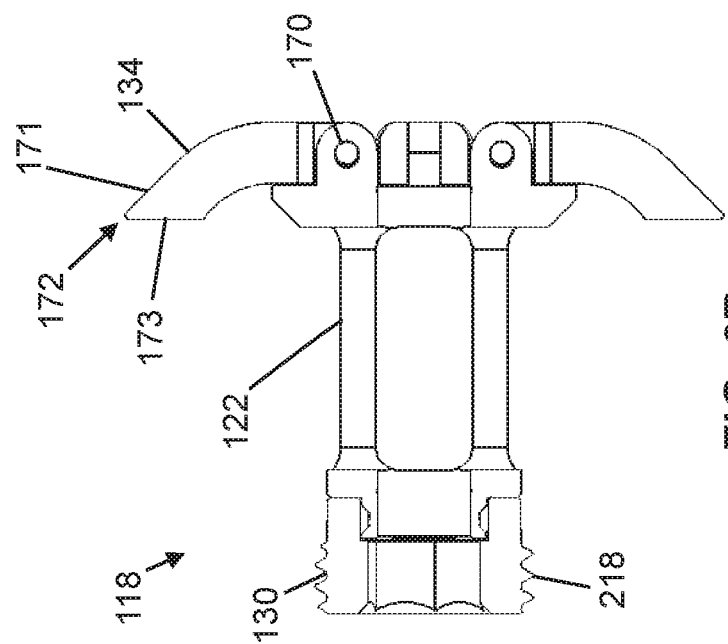
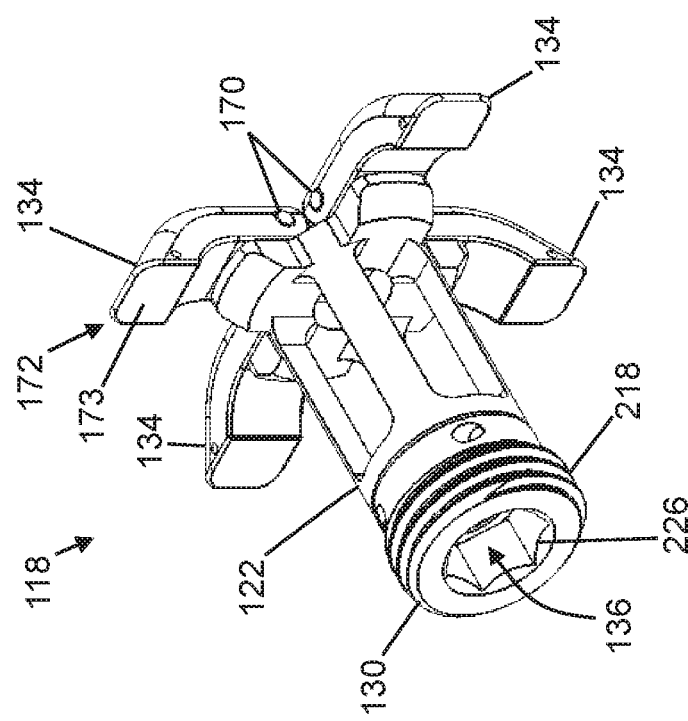
FIG. 6A
FIG. 6B

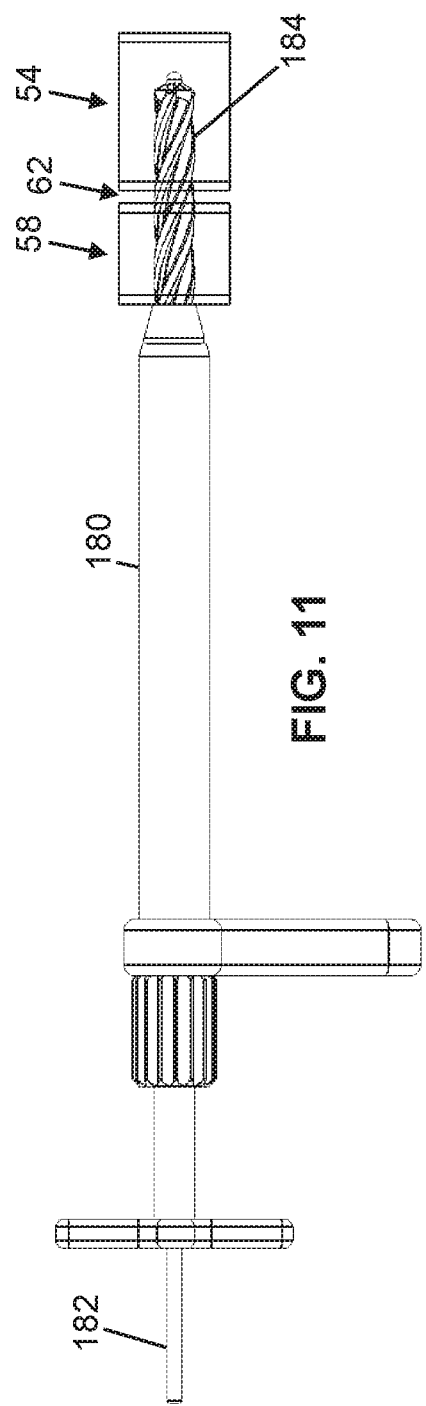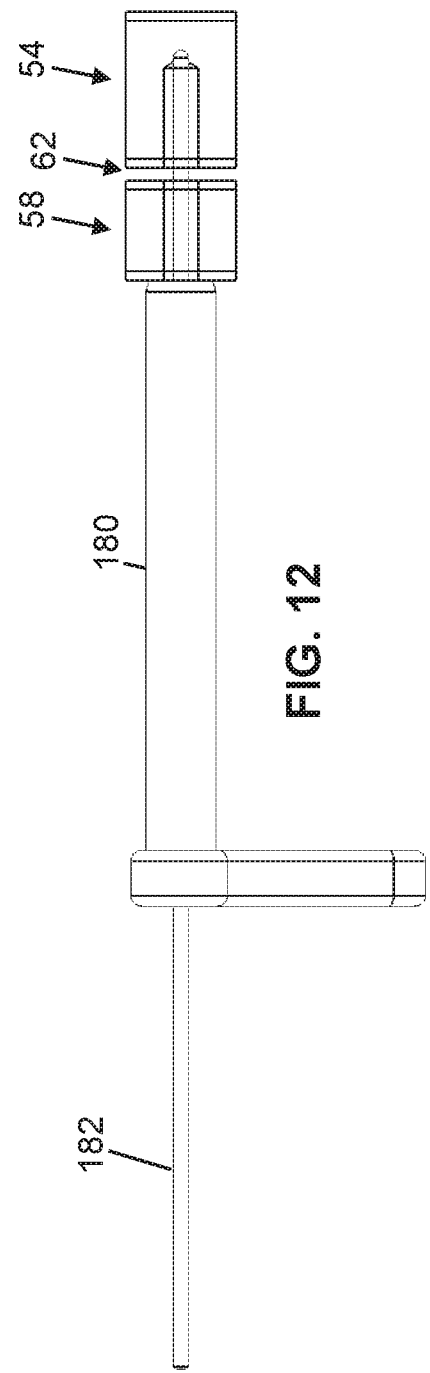

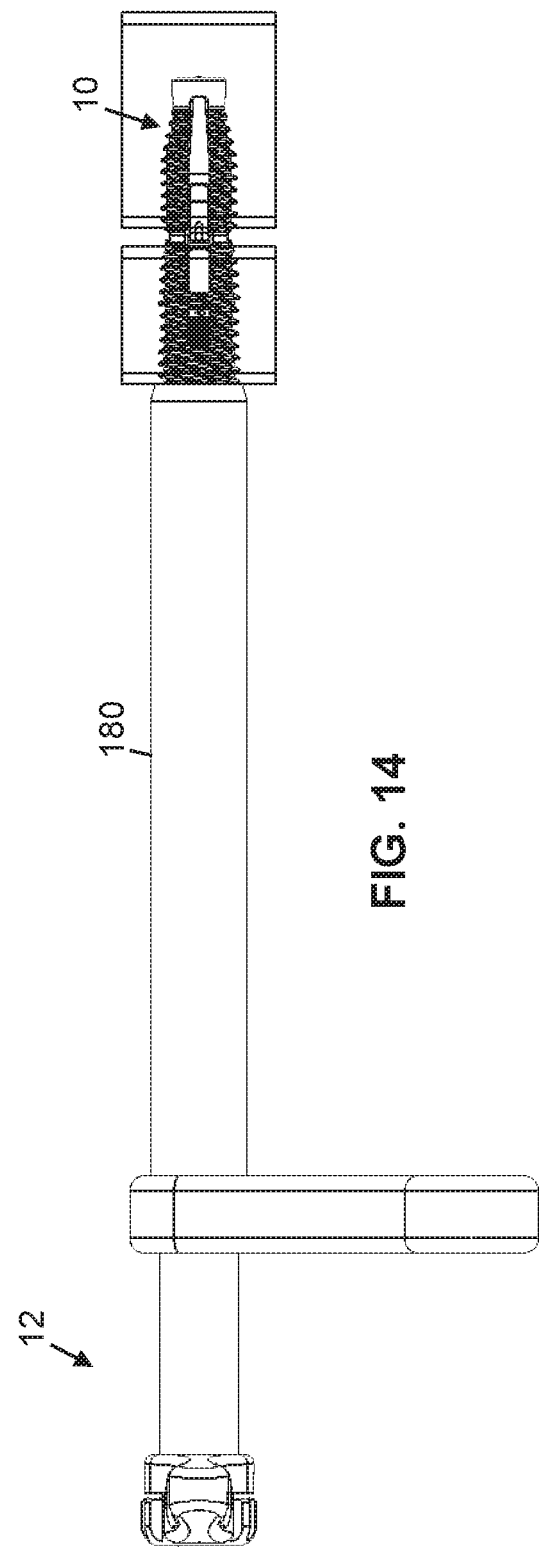

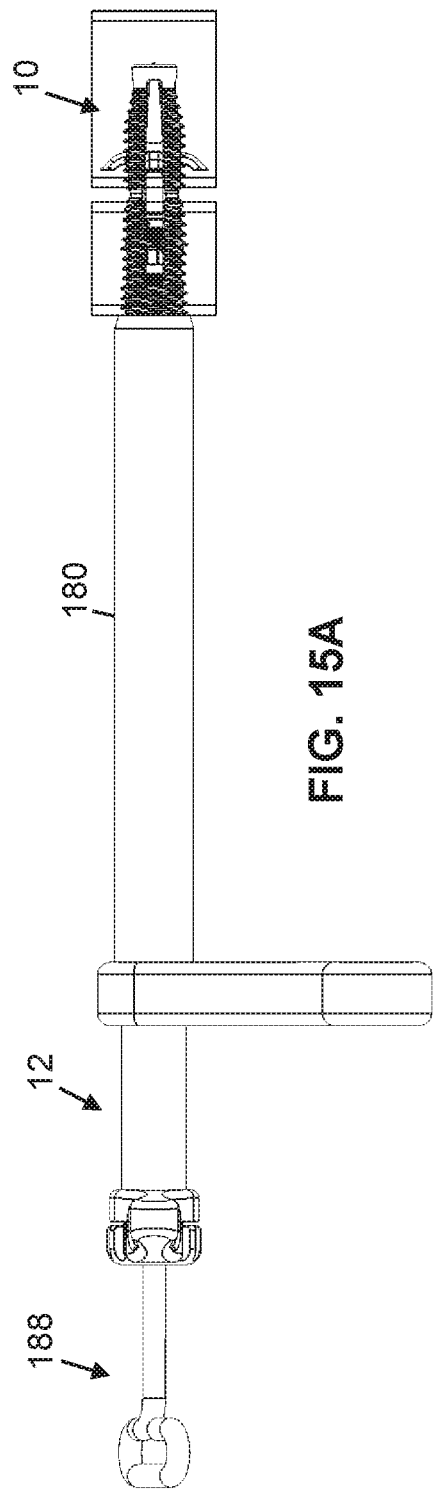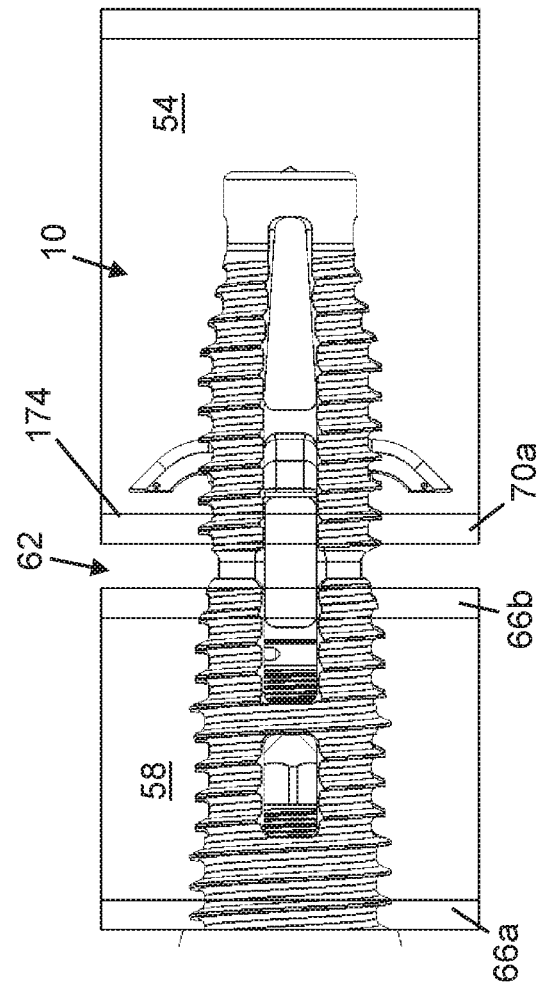
FIG. 15A
FIG. 15B

SACROILIAC JOINT STABILIZATION AND FIXATION DEVICES AND RELATED METHODS

CROSS-REFERENCE TO RELATED APPLICATIONS

The application claims priority to U.S. Provisional Application No. 62/622,649, filed Jan. 26, 2018, the entire contents of which is specifically incorporated by reference herein without disclaimer.

BACKGROUND OF THE INVENTION

1. Field of the Invention

The present invention relates generally to joint fixation devices, and more particularly, but not by way of limitation, to sacroiliac joint fixation devices and related methods.

2. Description of Related Art

The sacroiliac joint is a strong, weight-bearing synovial joint and part of the pelvis. The joint is comprised of strong ligamentous attachments and two articular dense cortical surfaces: the sacrum and the ileum. The body of both the sacrum and the ileum consists of soft cancellous bone.

The sacroiliac joint has been identified as a source of pain and disability in a large number of patients. Pain of the sacroiliac joint may be a result of bone degeneration, fracture, dislocation, and/or trauma. Current treatment management options include sacroiliac joint fusion. Traditional open surgical techniques for sacroiliac joint fusion carry a significant risk for complications. Percutaneous sacroiliac joint fusion, however, has emerged as a minimally invasive option for treating sacroiliac joint pain. Most percutaneous sacroiliac joint fixation techniques include passing a Kirschner wire ("K-wire") or Steinmann pin through the ilium into the sacrum via a lateral approach, followed by bone site preparation and placement of one or more fixation devices. These fixation devices may include a variety of longitudinal screws and/or triangular implants that are configured to be passed across the sacroiliac joint and anchored into the soft cancellous bone of the sacrum. Thereafter, bone graft may be placed into the sacroiliac joint to promote fusion.

A disadvantage, however, of these devices is the reliance on screw thread fixation and/or a simple compression fit in the soft cancellous bone of the sacrum. Therefore, there remains a need for sacroiliac joint stabilization fixation devices with improved sacral anchoring to provide better long-term compression of the joint space.

SUMMARY OF THE INVENTION

The embodiments described herein include the benefits of provide strong constructs that can sustain the weight of the patient's body, resist rotational and translational forces across the SI joint, promote sacroiliac joint fusion over time, and/or take advantage of the sacral cortical layer to resist pull-out. Furthermore, the embodiments described herein include the benefit of a reduced overall outer diameter of the device and a reduced overall length such that multiple devices may be placed closer together and such that the incision needed to insert the device is minimized.

Some embodiments of the present anchor devices, which are configured for use in sacroiliac joint stabilization, comprise a housing having one or more apertures; one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures; wherein, when the at least one of the one or more engagement members is in the extended position, the at least one of the one or more engagement members is configured to move to the extended position within cancellous bone of a sacrum; and wherein the anchor device comprises a continuous channel extending from a first end of the anchor device to a second end of the anchor device, the channel being configured to receive a guidewire.

In some embodiments, the housing comprises a first anchor defining the first end of the housing; and a second anchor defining the second end of the housing, the second anchor being longitudinally movable relative to the first anchor.

Some embodiments of the present anchors comprise a carriage assembly disposed in the second anchor, the carriage assembly comprising: the one or more engagement members, and an actuating screw movable in the bore of the housing and configured to effectuate movement of the at least one of the one or more engagement members between the retracted position and the extended position. In some embodiments, the actuating screw is configured to engage and translationally move a carriage housing in order to effectuate movement of the at least one of the one or more engagement members between the retracted position and the extended position. In some embodiments, the actuating screw is configured to mate with a threaded inner surface of the housing.

In some embodiments, the at least one of the one or more engagement members is rotatable between the retracted position and the extended position. In some embodiments, the at least one of the one or more engagement members is rotatable toward a cortical wall of the sacrum. In some embodiments, the at least one of the one or more engagement members comprises a contact surface configured to compress cancellous bone against an inner surface of a cortical wall of the sacrum when the engagement member is in the extended position. In some embodiments, the at least one one of the one or more engagement members comprises a contact surface configured to contact an inner surface of a cortical wall of the sacrum when the engagement member is in the extended position.

In some embodiments, at least a portion of the housing comprises a threaded outer surface; and when the at least one of the one or more engagement members is in the extended position, the contact surface is spaced a distance from the threaded outer surface, the distance being at least greater than the largest depth of the threads of the threaded outer surface.

In some embodiments, the one or more engagement members are longitudinally movable relative to the housing.

In some embodiments, wherein the housing comprises a first end and a second end, the second end having a diameter at least 10 percent smaller than the housing's largest diameter.

Some embodiments of the present assemblies for use in sacroiliac joint ("SI joint") stabilization comprise one or more of the present anchor devices and a driver tool configured to thread the device across the SI joint. In some embodiments, the driver tool includes a cannula coupled to a handle, the cannula and the handle each defining a channel configured to receive a guidewire.

Some embodiments of the present methods of using an anchor device to stabilize a sacroiliac joint ("SI joint") comprise inserting a guidewire across an SI joint such that the guidewire extends through an ilium and at least partially into a sacrum; positioning an anchor device over the guidewire, where the anchor device includes: a housing, wherein the housing comprises: an inner anchor; an outer anchor; and one or more apertures; one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures; wherein the anchor device comprises a continuous channel extending from a first end of the anchor device to a second end of the anchor device, the channel being configured to receive the guidewire; moving the anchor device across the SI joint such that the device extends through the ilium and at least partially into the sacrum; moving an actuating screw in the channel of the housing toward the second end of the anchor device, thereby causing longitudinal movement of the at least one of the one or more engagement members; rotating the at least one of the one or more engagement members from the retracted position to the extended position, wherein the at least one of the one or more engagement members move to the extended position within cancellous bone of the sacrum; and urging, when the at least one of the one or more engagement members is in the extended position, the inner anchor towards the outer anchor to reduce a width of the SI joint.

In some embodiments, moving the actuating screw in the channel causes the rotation of the at least one of the one or more engagement members from the retracted position to the extended position.

In some embodiments, when the anchor device is positioned across the SI joint, the one or more engagement members are longitudinally spaced from the cortical wall of the sacrum by a distance such that the at least one of the one or more engagement members are movable to the extended position.

Some embodiments include positioning a tissue shield over the guidewire before positioning the anchor device over the guidewire.

Some embodiments include enlarging a space around the guidewire after the guidewire has been inserted across the SI joint.

Some embodiments include inserting a second guidewire across the SI joint such that the guidewire extends through the ilium and at least partially into the sacrum; positioning a second anchor device over the second guidewire, where the second anchor device includes: a second housing, wherein the second housing comprises: an inner anchor; an outer anchor; and one or more apertures; one or more engagement members at least partially disposed in the second housing, where at least one of the one or more engagement members is movable between a retracted position and an extended position such that, when the at least one of the one or more engagement members is in the extended position, the at least one of the one or more engagement members extends through at least one of the one or more apertures; wherein the second anchor device comprises a continuous channel extending from a first end of the anchor second device to a second end of the anchor second device, the channel being configured to receive the second guidewire; moving the second anchor device across the SI joint such that the second anchor device extends through the ilium and at least partially into the sacrum; moving a second actuating screw in the channel of the second housing toward the second end of the second anchor device, thereby causing longitudinal movement of the at least one of the one or more engagement members; rotating the at least one of the one or more engagement members of the second anchor device from the retracted position to the extended position, wherein the at least one of the one or more engagement members move to the extended position within cancellous bone of the sacrum; urging, when the at least one of the one or more engagement members of the second anchor device is in the extended position, the inner anchor of the second anchor device towards the outer anchor of the second anchor device to reduce a width of the SI joint; and urging, when the at least one of the one or more engagement members of the anchor device is in the extended position, the inner anchor of the anchor device towards the outer anchor of the anchor device to reduce a width of the SI joint.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the devices, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A-4D are perspective, first side, second side, and third side views of the inner anchor of FIGS. 3A and 3B.

FIGS. 6A and 6B are perspective and cross-section views of a carriage assembly suitable for use in some embodiments of the present anchor devices, shown with a carriage housing, an actuating screw, and a plurality of engagement members.

FIGS. 8-16B are various views of an embodiment of a method for using the present assemblies.

DESCRIPTION OF ILLUSTRATIVE EMBODIMENTS

Figure 1:
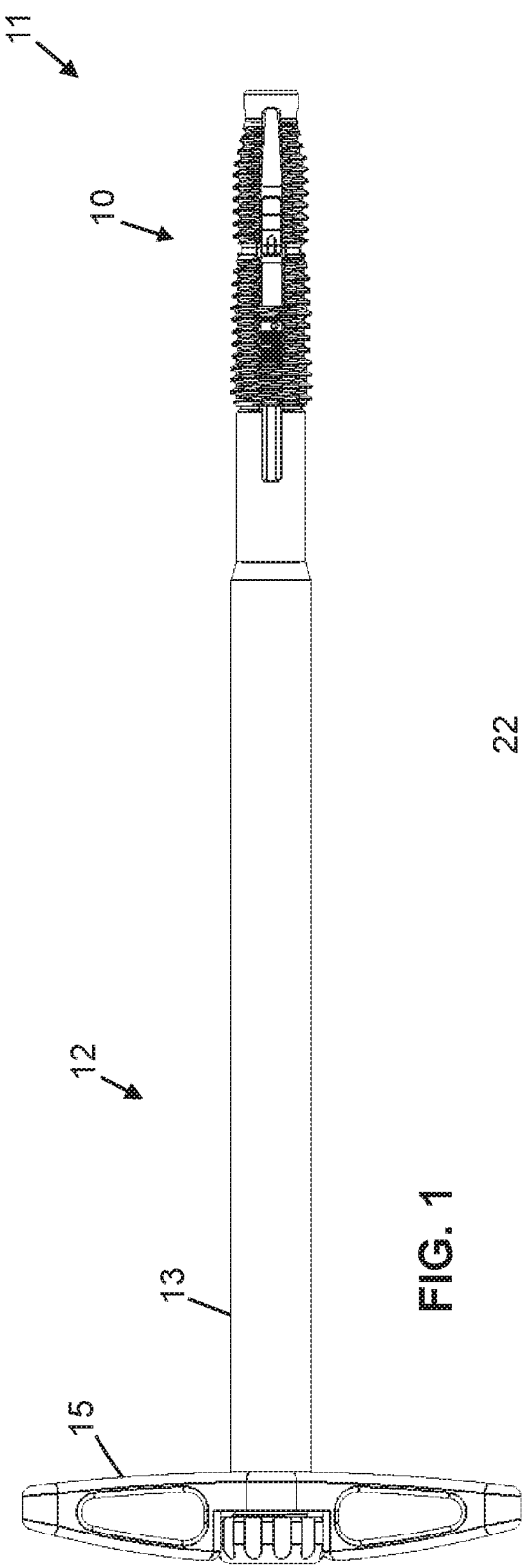
FIG. 1 is a side view of one embodiment of the present assemblies, shown with one embodiment of the present anchor devices.
Figure 2A:
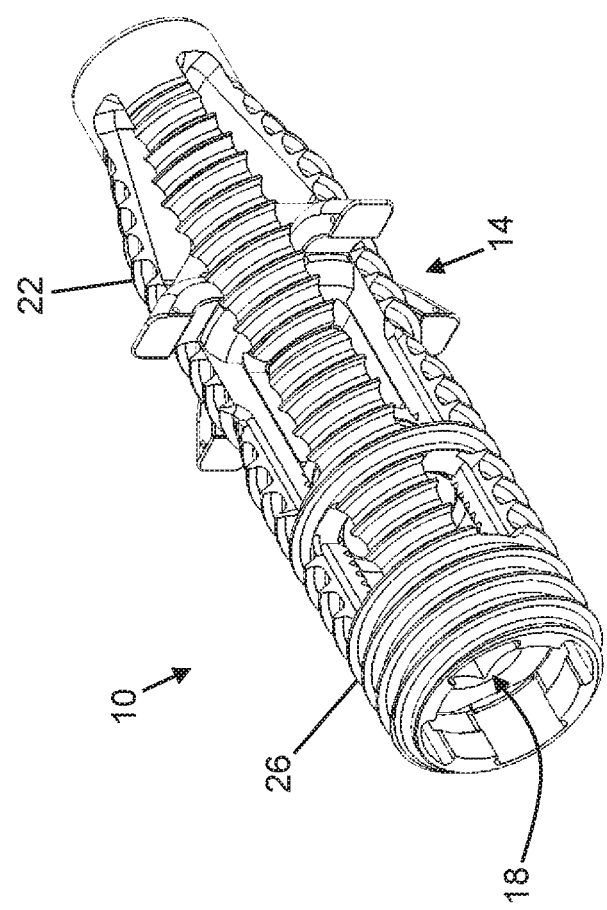
FIGS. 2A-2E are perspective, first side, second side, third side, and cross-section views of the anchor device of FIG. 1.
Figure 2B:
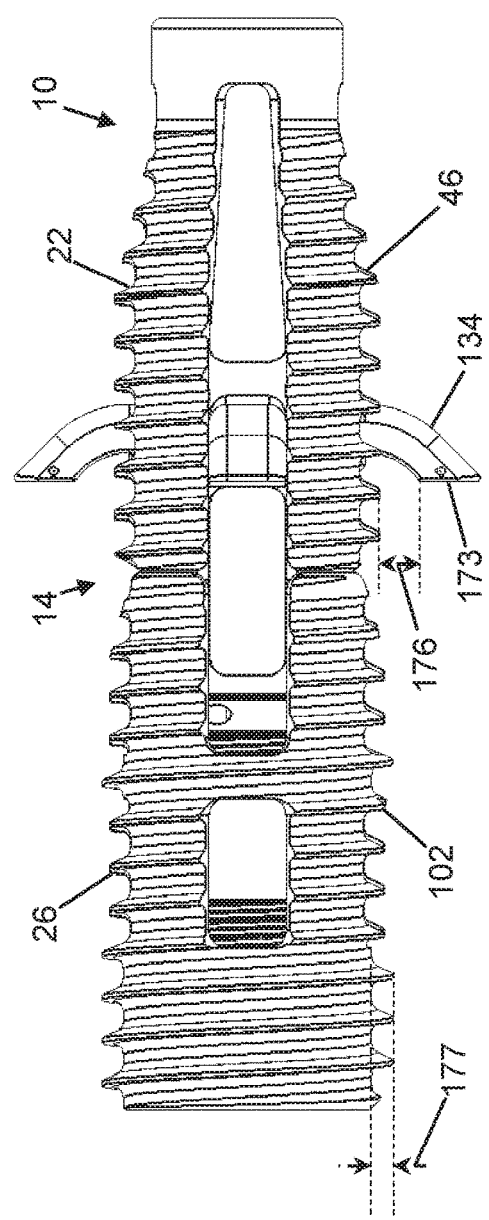
Figure 2D:
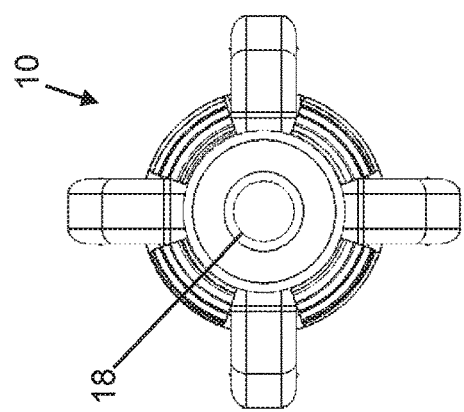
Figure 2C:
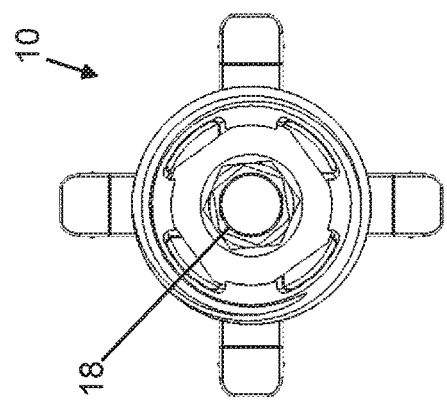
Figure 2E:
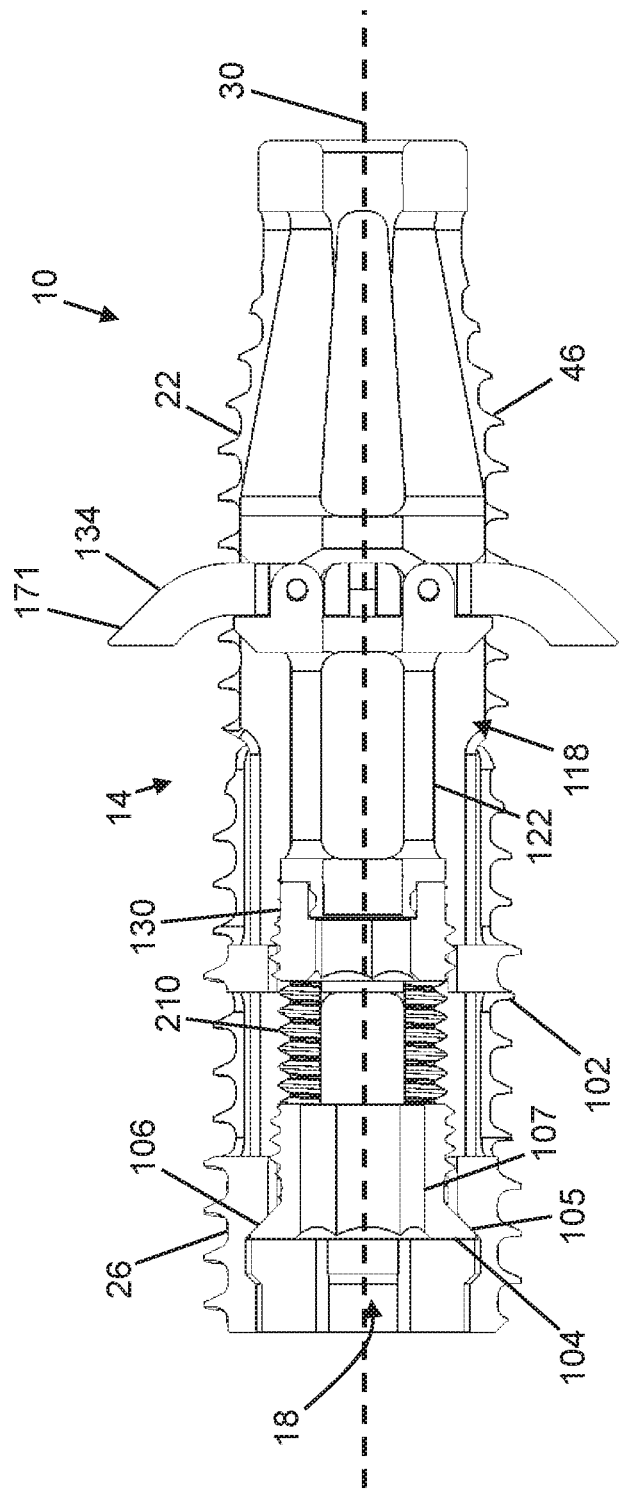
Figure 16A:
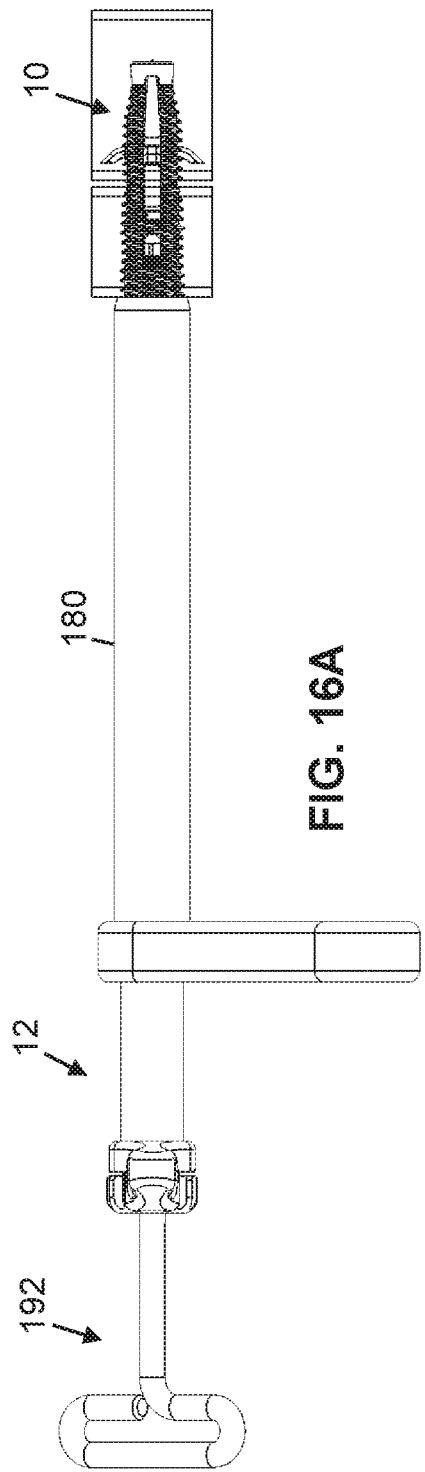

Referring now to the drawings, and more particularly to FIGS. 1-2E, shown therein and designated by the reference numeral 10 is one embodiment of the present anchor devices. Device 10 can be a component in an anchor assembly 11 that includes a driver tool 12 having a cannula 13 coupled to a handle 15. Device 10 may be removably coupled to cannula 13 such that, when the device is appropriately positioned across a sacroiliac joint ("SI joint") (e.g., 62) (FIGS. 16A and 16B), the cannula can be detached from the device.

In the embodiment shown, device 10 includes an elongated housing 14 having a channel 18 extending therethrough. In the depicted embodiment, housing 14 comprises an inner anchor 22 movable (e.g., axially) relative to an outer anchor 26. In this embodiment, components of device 10 may be characterized by and described relative to a longitudinal axis 30 extending along a length thereof.

Figure 16B:
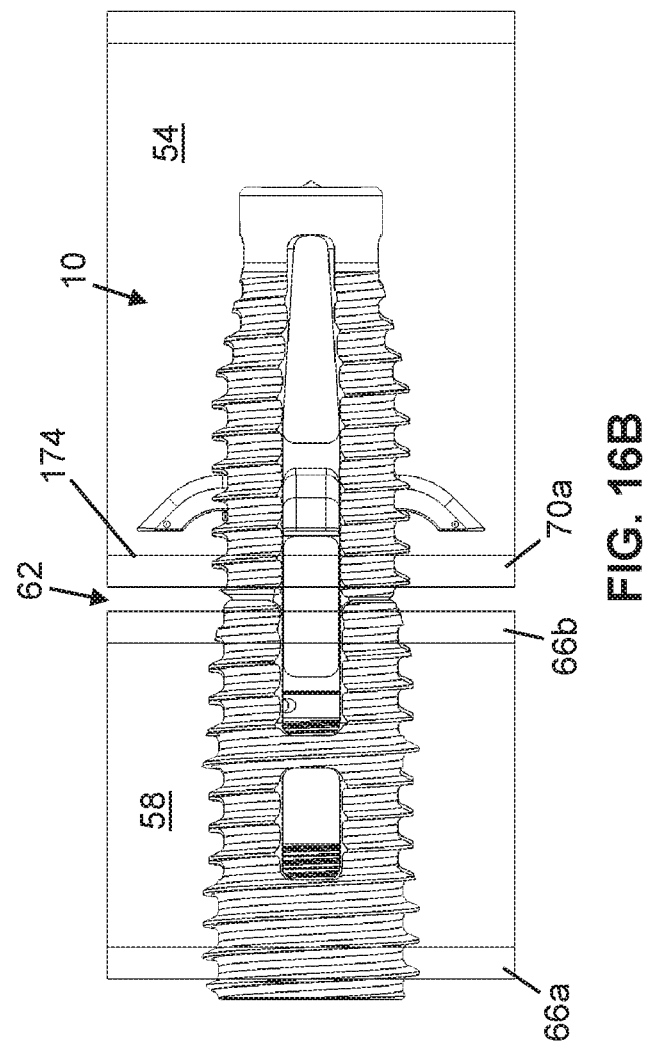

Referring specifically to FIGS. 4A-4D, inner anchor 22 includes a first end 34, a second end 38, and a channel 42 extending between the first end and the second end. Channel 42 is concentric with channel 18 of housing 14. As shown, inner anchor 22 includes a threaded outer surface 46. Referring additionally to FIGS. 15B and 16B, shown therein is device 10 disposed within a sacrum bone 54 and an iliac bone 58, wherein the device extends across an SI joint 62 between the sacrum and the ilium. In this embodiment, at least a portion of threaded outer surface 46 of inner anchor 22 may be configured to be threaded through an outer cortical wall 66a and an inner cortical wall 66b of iliac bone 58 ("iliac cortical wall") and/or a cortical wall 70a of sacrum bone 54 ("sacral cortical wall"). As described in further detail below, to facilitate and assist the threading of inner anchor 22 into cortical walls 66a and 66b of ilium 58 and cortical wall 70a of sacrum 54, second end 38 of the inner anchor may comprise an outer diameter 71 that is at least approximately 10 percent (e.g., at least approximately any one of or between approximately any two of the following: 10, 15, 20, 25, 30, 35, 40, 45, 50 percent) less than the inner anchor's largest outer diameter 72. As shown, second end 38 of inner anchor 22 can comprise an non-threaded outer surface 74 and/or a chamfered or rounded leading edge 75 to facilitate threading of device 10.

In the embodiment shown, at least a portion of inner anchor 22 may include a non-threaded outer surface 78 configured to contact a non-threaded inner surface of outer anchor 26. In the depicted embodiment, non-threaded outer surface 78 of inner anchor 22 can be defined by two or more fingers 80 extending in a direction parallel to longitudinal axis 30. As shown, one or more fingers 80 can cooperate to define a threaded inner surface 210 of inner anchor 22. Non-threaded outer surface 78 may comprise an axial length at least as long as the width of SI joint 62.

Referring specifically to FIGS. 5A-5D, outer anchor 26 includes a first end 90, a second end 94, and a channel 98 extending between the first end and the second end. Channel 98 is concentric with channel 18 of housing 14. As shown in FIGS. 2E and 3B, first end 34 of inner anchor 22 may be at least partially disposed within channel 98 of outer anchor 26. At least a portion of outer anchor 26 may include a threaded outer surface 102 configured to be threaded into cortical walls 66a and/or 66b of ilium 58 such that axial (e.g., translational) movement of the outer anchor relative to SI joint 62 is thereby restricted. As shown, at least a portion of threaded outer surface 102 of outer anchor 26 can be defined by two or more fingers 103 extending in a direction parallel to longitudinal axis 30.

As shown in FIG. 2E, inner anchor 22 may be secured to outer anchor 26 by a compression screw 104. For example, compression screw 104 may be at least partially disposed within channel 98 of outer anchor 26. Compression screw 104 comprises a head 105 configured to contact a shoulder 106 of outer anchor 26 to prevent the removal of the compression screw out of channel 98 at second end 94. Compression screw 104 may be configured to be threaded with threaded inner surface 210 of inner anchor 22. As such, compression screw 104 secures inner anchor 22 with outer anchor 26. Compression screw 104 may also cause inner anchor 22 to move relative to outer anchor 26. For example, by threading compression screw 104 along threaded inner surface 210 of inner anchor 22, the compression screw causes the inner anchor to move toward outer anchor 26 (i.e., further into channel 98). As discussed in herein, when device 10 is disposed across an SI joint (e.g., 62), movement of inner anchor 22 toward outer anchor 26 can cause a reduction in the width (i.e., compression) of the SI joint. As shown, compression screw 104 comprises a channel 107 configured to accommodate a guidewire (e.g., 178, 182), as discussed in further detail herein.

Threaded outer surface 102 of outer anchor 26 may be timed with threaded outer surface 46 of inner anchor 22 such that, for example, a single thread groove is formed in iliac cortical walls 66a and 66b and/or sacral cortical wall 70a when device 10 is positioned across SI joint 62. As shown, threaded outer surface 102 of outer anchor 26 and/or threaded outer surface 46 of inner anchor 22 may include a single-start thread. In some embodiments, a threaded outer surface (e.g., 102) of an outer anchor (e.g., 26) and/or a threaded outer surface (e.g., 46) of an inner anchor (e.g., 22) may include any appropriate thread start, such as, for example, a double-start thread or a triple-start thread.

Figure 3A:
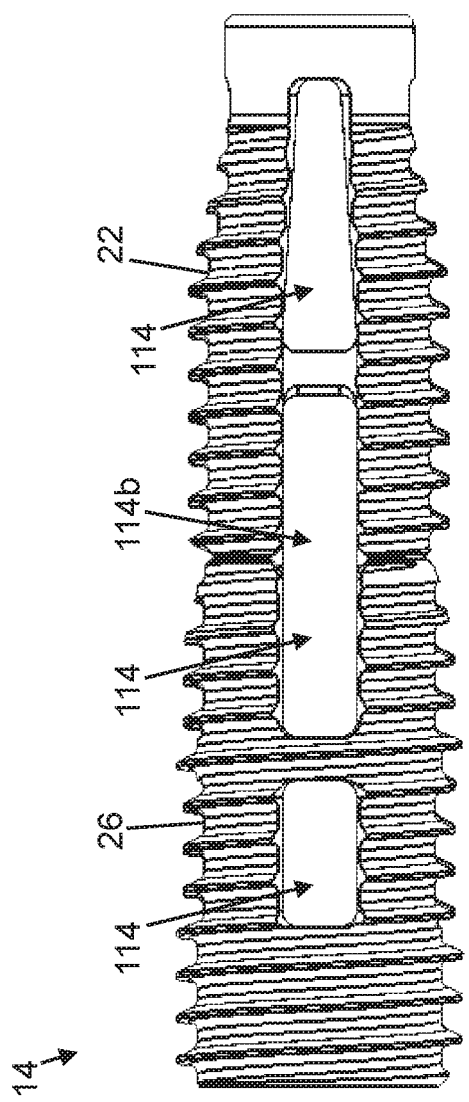
FIGS. 3A and 3B are side and cross-section views of a housing suitable for use with some embodiments of the present anchor devices, shown with an inner anchor and an outer anchor.
Figure 3B:
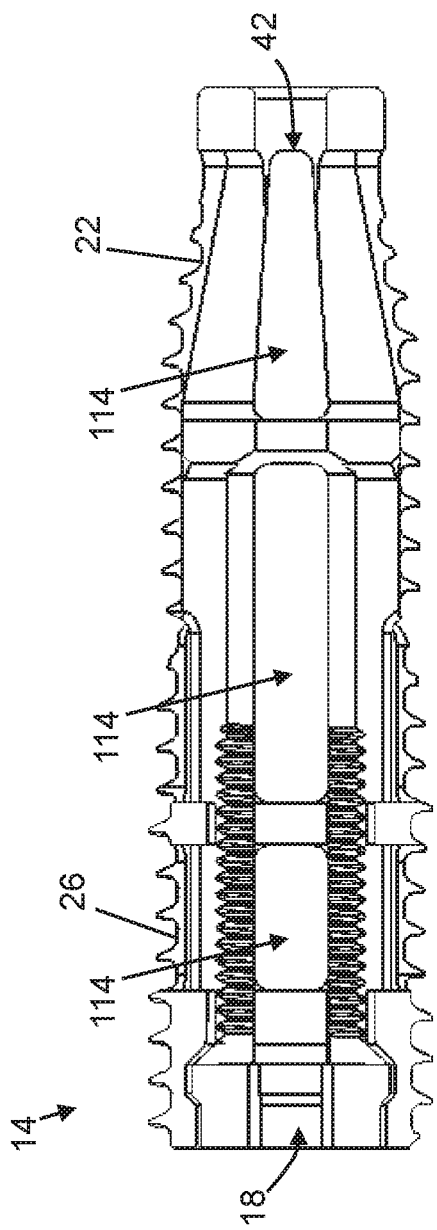
Figure 5C:
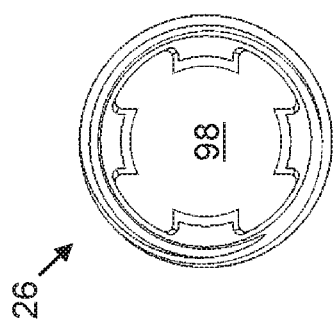
FIGS. 5A-5D are perspective, first side, second side, and third side views of the outer anchor of FIGS. 3A and 3B.
Figure 5D:
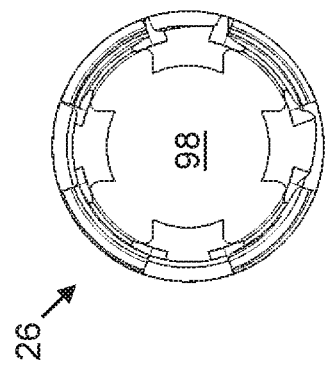
Figure 5A:
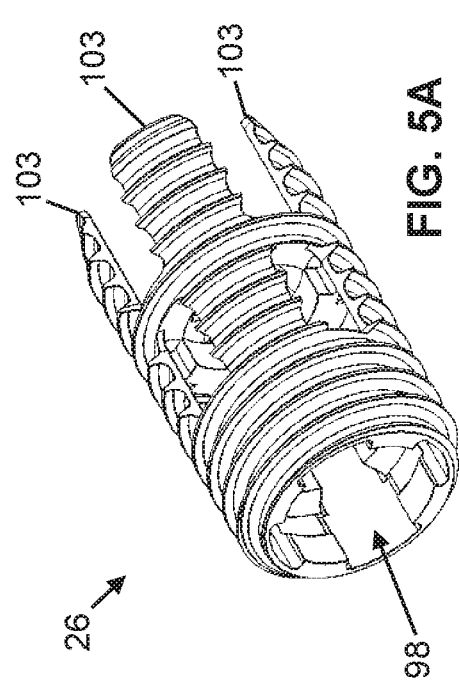
Figure 5B:
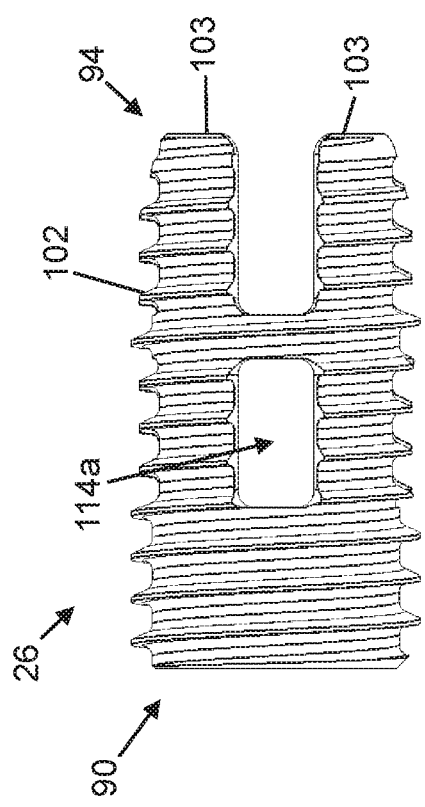
Figure 7C:
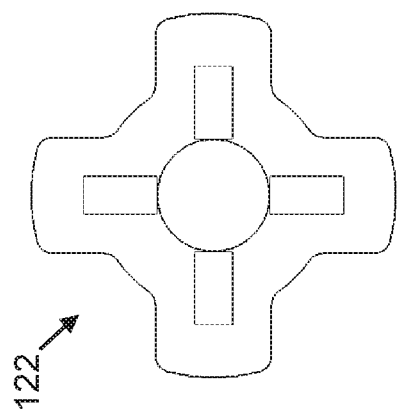
FIGS. 7A-7D are perspective, first side, second side, and third side views of the carriage housing of FIGS. 6A and 6B.
Figure 7D:
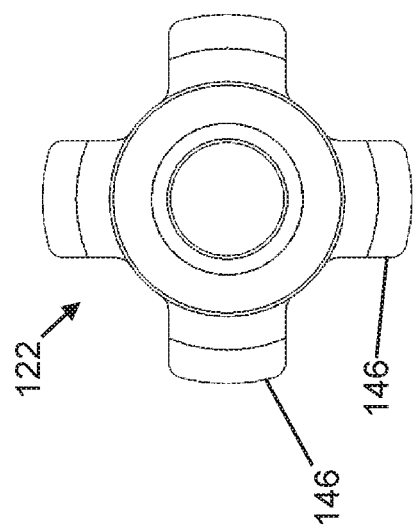
Figure 7A:
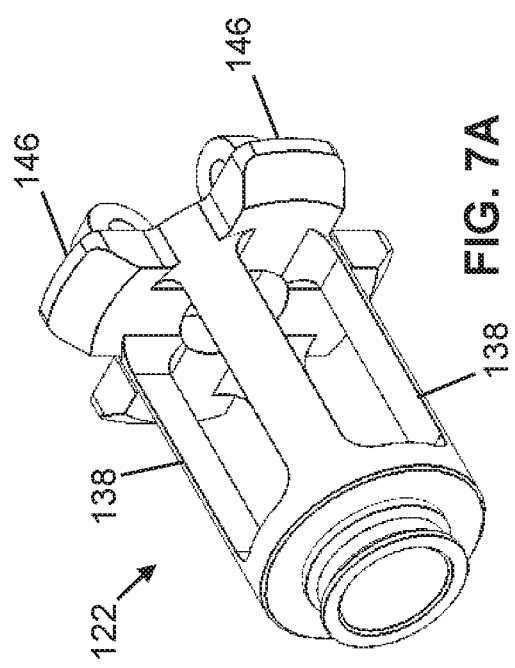
Figure 7B:
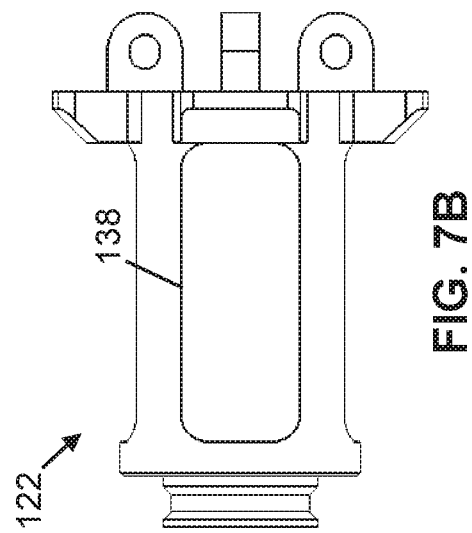
Figure 8:
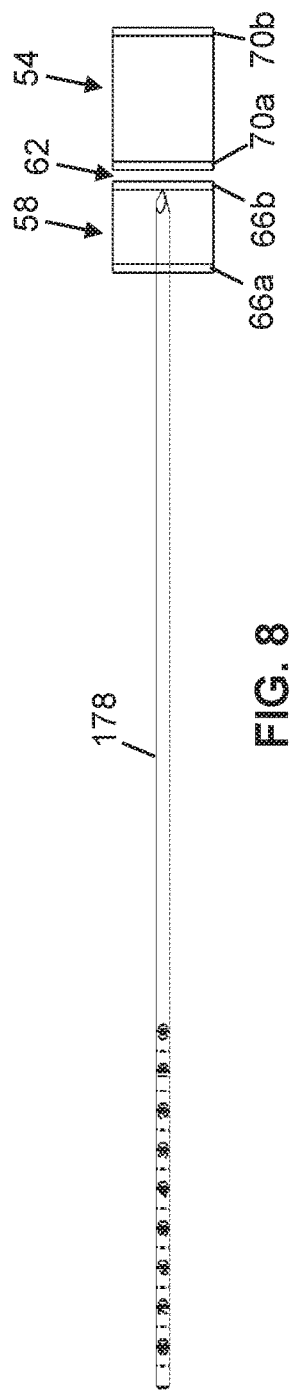

Referring specifically to FIGS. 3A and 3B, housing 14 may be configured to include one or more sets of apertures 114 (e.g., three sets of apertures, as shown), wherein each set is axially spaced apart from an adjacent set by at least approximately one millimeter (e.g., at least approximately 1, 2, 3, 4, 5 or more millimeters). Each set of apertures 114 can comprise one or more apertures, circumferentially spaced about device 10 (in embodiments where the device includes a plurality of apertures). One or more sets of apertures 114 may be defined by inner anchor 22, outer anchor 26, and/or a combination of the inner anchor and the outer anchor. For example, outer anchor 26 defines a first set of apertures 114a (FIG. 5B). Outer anchor 26 and inner anchor 22 cooperate to define a second set of apertures 114b (FIG. 3A), between respective fingers 80 and 103 of the outer anchor and the inner anchor. Device 10 comprises a third set of apertures 114c defined by inner anchor 22 (FIG. 4B). One or more sets of apertures 114 can be configured to facilitate the injection of fixation material, such as bone graft, bone cement, and/or the like into sacrum 54, ilium 58, and/or SI joint 62 through one or more apertures of the set.

Referring additionally to FIGS. 6A-7D, device 10 includes a carriage assembly 118 movable within channel 18 of housing 14. As shown, carriage assembly 118 includes a carriage housing 122, an actuating screw 130, and one or more engagement member(s) 134 (e.g., four (4) engagement members, as shown) coupled to the carriage housing. As shown, carriage assembly 118 defines a channel 136 that is concentric with channel 18 of housing 14.

Carriage housing 122 may include one or more carriage apertures 138 (e.g., four (4) carriage apertures, as shown) to facilitate the injection of fixation material, such as, for example, bone graft, bone cement, and/or the like into sacrum 54, ilium 58, or SI joint 62 via the aperture. Apertures 138 are configured to be circumferentially aligned with at least one set of apertures 114 of housing 14. In this embodiment, carriage housing 122 and inner anchor 22 may be configured to cooperate to prevent rotational movement and/or axial translational movement of the carriage housing relative to the inner anchor, thereby preventing circumferential misalignment of a respective set of apertures 114 of housing 14 and carriage apertures 138 of carriage housing 122. For example, in the embodiment shown, carriage housing 122 may include one or more protrusion(s) 146 extending radially outward relative to longitudinal axis 30 and configured to be keyed into corresponding alignment slot(s) 150 defined by housing 14, such as, for example, inner anchor 22 (e.g., FIG. 4C).

Actuating screw 130 may be configured to effectuate translational movement of carriage housing 122 along longitudinal axis 30. For example, actuating screw 130 may comprise a threaded outer surface 218 configured to mate with a threaded inner surface 210 of inner anchor 22 such that the actuating screw may be threaded along channel 18 of housing 14. As actuating screw 130 is threaded along channel 18 of housing 14, the actuating screw contacts carriage housing 122 and translationally moves the carriage housing along the channel towards second end 38 of inner anchor 22. For example, actuating screw 130 includes a cap portion 226 configured to receive an actuation tool (e.g., 188), which is removably insertable into channel 18 of housing 14 to thread the actuating screw through the channel.

By effectuating translational movement of carriage housing 122 along longitudinal axis 30 toward second end 38 of inner anchor 22, actuating screw 130 can effectuate movement of one or more engagement member(s) 134 between a retracted position and an extended position. In the retracted position, engagement member 134 may be configured to extend a first distance from longitudinal axis 30. In the extended position, engagement member 134 may be configured to extend a second distance from longitudinal axis 30, where the second distance is greater than the first distance. For example, one or more engagement members 134 may be hingedly coupled to carriage housing 122 (e.g., via a hinge 170) such that the engagement member is rotatable between the retracted and the extended positions. When in the extended position, one or more engagement members 134 may be configured to extend through a respective aperture in a set of apertures 114 of housing 14.

One or more engagement members 134 may include any suitable shape such that translational movement of the engagement member toward second end 38 of inner anchor 22 (e.g., caused by translational movement of actuating screw 130 and/or carriage housing 122) causes the engagement member to move from the retracted position to the extended position. For example, one or more engagement members 134 may comprise a rounded or tapered contact surface 171 configured to contact inner anchor 22 as the engagement member moves toward second end 38 of the inner anchor. Contact between surface 171 of engagement member 134, while the engagement member translationally moves toward second end 38, can cause the engagement member to rotate about hinge 170 and thereby move toward the extended position.

During use, device 10 may be disposed across SI joint 62 and extend at least partially into sacrum 54 such that one or more engagement members 134 may be actuated to anchor housing 14 against sacral cortical wall 70a. For example, device 10 may be aligned relative to SI joint 62 such that one or more engagement members 134 can be actuated to extend into the cancellous bone of sacrum 54. As engagement member 134 rotates about hinge 170 toward the extended position, an end 172 of the engagement member opposite the hinge moves toward SI joint 62. As such, as engagement member 134 rotates about hinge 170 toward the extended position, a contact surface 173 at end 172 of the engagement member compresses cancellous bone within sacrum 54 against an inner surface 174 of sacral cortical wall 70a. Thus, when engagement member 134 is in the extended position, end 172 of the engagement member may be in contact with compressed cancellous bone (i.e., compressed between inner surface 174 of sacral cortical wall 70a and contact surface 173) to secure device 10 across SI joint 62 and within the sacrum, as shown in FIG. 15B. In some embodiments, a contact surface (e.g., 173) of at least one engagement member (e.g., 134) may be in direct contact with an inner surface (e.g., 174) of a sacral cortical wall (e.g., 70a) when the engagement member is in the extended position. As shown, contact surface 173 can be substantially planar. In some embodiments, a contact surface (e.g., 173) of at least one engagement member (e.g., 134) may be textured, smooth, and/or rounded.

As shown in FIG. 2B, when engagement member 134 is in the extended position, contact surface 173 is spaced a distance 176 from a threaded outer surface (e.g., 46, 102). Distance 176 may be equal to or greater than (e.g., two or three times greater than) a depth 177 of the threads of threaded outer surface (e.g., 46, 102), and, if the depth of the threads varies along a length of housing 14, equal to or greater than a deepest depth (e.g., 177) of the threads of threaded outer surface (e.g., 46, 102). By spacing contact surface 173 away from threaded outer portion (e.g., 46, 102), engagement members 134 can increase the anchor strength of the threaded outer portion.

One or more engagement members 134 may be hingedly coupled such that the engagement member moves uniaxially, biaxially, or multiaxially, thereby allowing the engagement member to adjust to irregularities and variable angles of inner surface 174 of sacral cortical wall 70*a* and/or compacted cancellous bone adjacent the sacral cortical wall.

One or more components of device 10 can comprise any suitable biocompatible material, such as plastic, stainless steel, rubber, titanium, and/or the like, that is manufactured using any suitable technique, such as machining, additive manufacturing, subtractive manufacturing, and/or the like.

Figure 9:
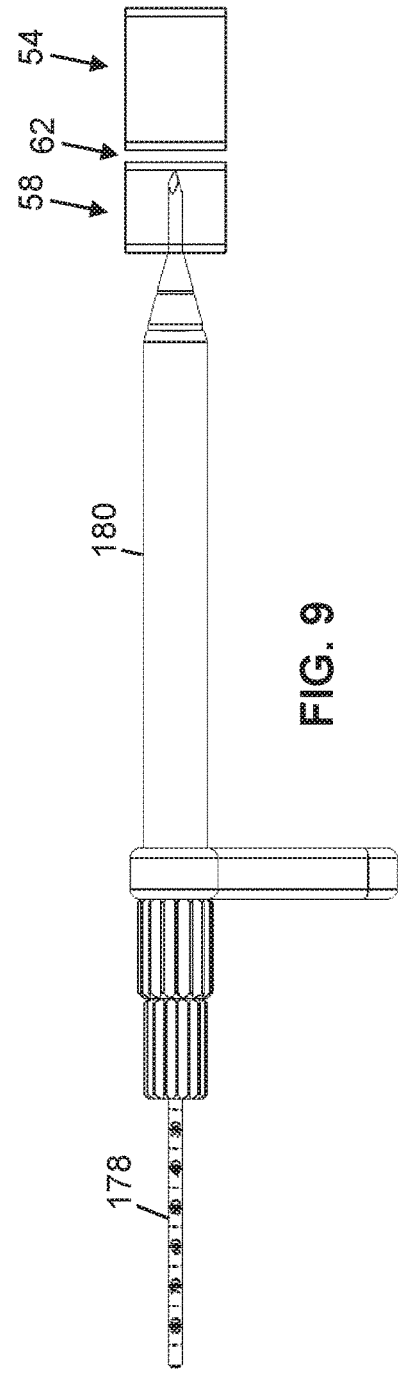
Figure 10:
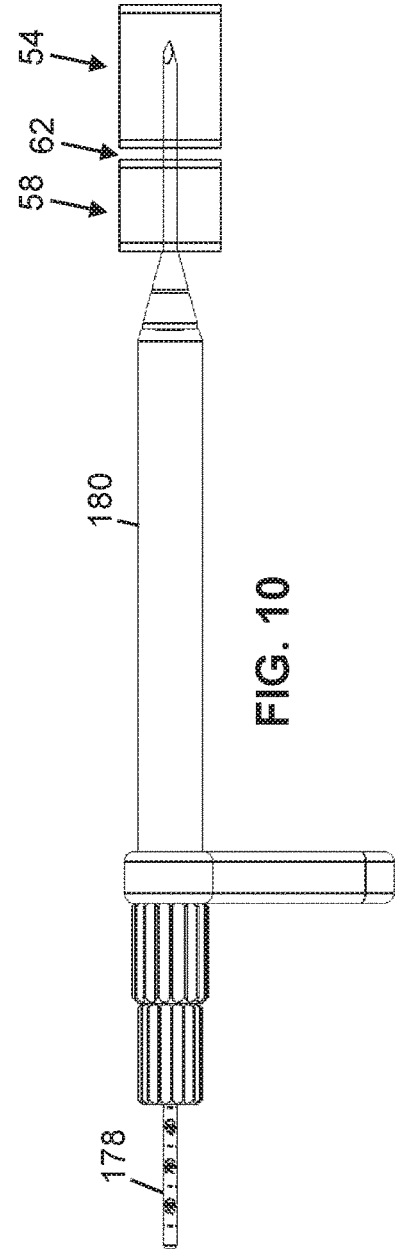

Referring additionally to FIGS. 8-16B, shown therein is the procedure for installing device 10 across SI joint 62. First, a sharp-tipped guidewire 178 (e.g., such as a Kirschner wire ("K-wire"), Steinmann pin, and/or the like) is inserted in a lateral trajectory such that the guidewire contacts inner cortical wall 66*b* of ilium 58. Then, as shown in FIG. 9, a tissue shield 180 is inserted over guidewire 178 and a depth of the guidewire is measured (via graduations on the guidewire). Next, as shown in FIG. 10, guidewire 178 is inserted in a lateral trajectory across ilium 58 and SI joint 62 and into sacrum 54 and the depth of the guidewire is again measured to prevent insertion through an inner cortical wall 70*b* of the sacrum.

Thereafter, as shown in FIGS. 11 and 12, a space around guidewire 178 may be enlarged using one or more drills bits (e.g., 184), taps, a combination thereof, and/or the like. In some embodiments, in preparation for bone placement, an SI joint (e.g., 62) may be at least partially cleared and/or cleaned using one or more (e.g., angled) curettes. During or after drilling with drill bit 184, sharp-tipped guidewire 178 can be removed and a blunt-tipped guidewire 182 can be inserted into across SI joint 62, in the position previously occupied by the sharp-tipped guidewire.

Figure 13A:
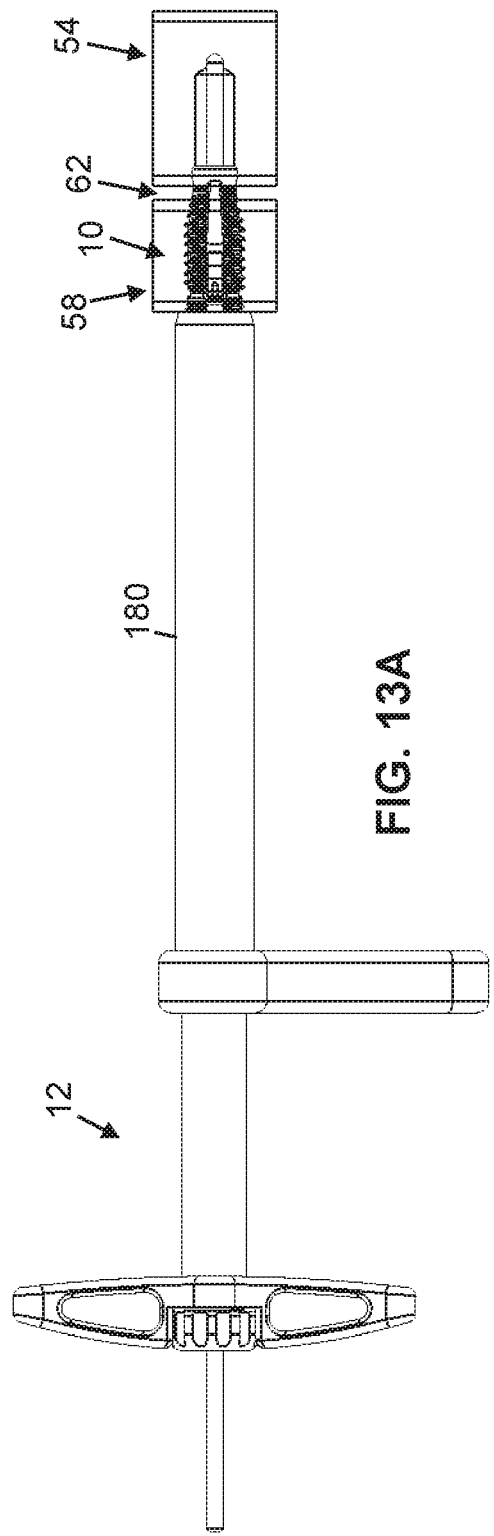
Figure 13B:
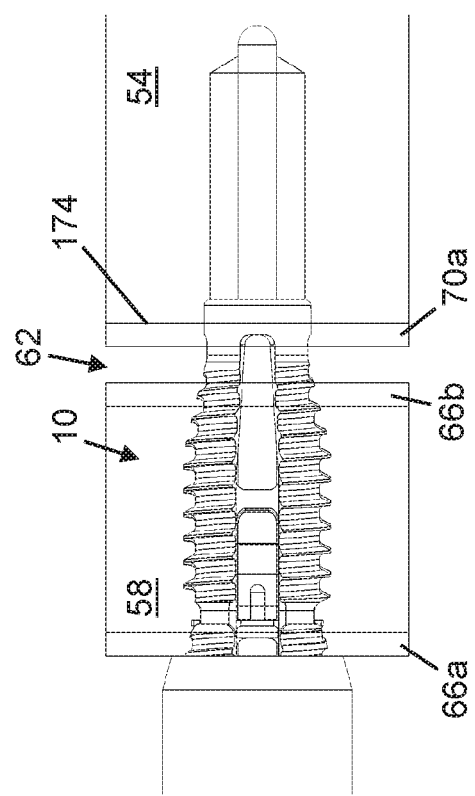

Next, an assembly (e.g., 11) which may be stored in a sterile container is removed from the container and fit onto guidewire 182 (FIG. 13A). As discussed above, channels 18, 42, 98, and 136 of device 10 are concentric and may be configured to accommodate and move relative to guidewire 182. As device 10 is moved over guidewire 182 toward SI joint 62, second end 38 of inner anchor 22, whose diameter 71 is smaller than diameter 72 and comprises non-threaded outer surface 74, may move into the space enlarged by one or more drill bits (e.g., 184) and thereby guide threaded outer surfaces 102 and 46 into threaded contact with cortical walls 66*a* and/or 66*b* and 70*a*, respectively (shown in greater detail in FIGS. 15B and 16B). As shown in FIG. 13A, driver tool 12 may be used to thread device 10 across SI joint 62.

Driver tool 12 may facilitate the positioning of device 10 across SI joint 62 such that threaded outer surface 102 of outer anchor 26 is threaded into inner cortical wall 66*b* of ilium 58 and threaded outer surface 46 of inner anchor 22 is threaded into outer cortical wall 70*a* of sacrum 54. When device 10 is in such a position across SI joint 62, contact surface 173 of one or more engagement members 134 is exposed to cancellous bone within sacrum 54, thereby allowing the engagement member to, upon actuation, move into the extended position within the sacrum.

Driver tool 12 may be configured to receive an actuation tool 188 (i.e., the driver tool may have a channel extending therethrough) to actuate one or more engagement members 134 between the retracted and extended positions. For example, actuation tool 188 is received by cap portion 226 of actuating screw 130 and, upon rotation of the actuation tool, causes carriage assembly 118 to translationally move toward second 38 of inner anchor 22. In turn, one or more engagement members 134 may be caused to contact inner anchor 22, which causes the engagement member to move toward the extended position (e.g., via contact between surface 171 and the inner anchor). In turn, one or more engagement members 134 compresses cancellous bone between sacral cortical wall 70*a* and contact surface 173 of the engagement member, thereby securing device 10 within sacrum 54.

Thereafter, actuation tool 188 is removed and a compression tool 192 is inserted into drive tool 12 to effectuate compression of SI joint 62. For example, compression tool 192 is received by compression screw 104, which, when threaded, causes inner anchor 22 and outer anchor 26 to move toward each other. At least because inner anchor 22 is threaded in sacral cortical wall 70*a* and anchored by one or more engagement member 134 within sacrum 54 and because outer anchor 26 is threaded in iliac cortical walls 66*a* and/or 66*b*, threading compression screw 104 causes the sacral cortical wall and the iliac cortical wall to move closer toward each other as well, thereby reducing the width of SI joint 62 (compare FIGS. 15A and 15B with FIGS. 16A and 16B).

In some embodiments, multiple devices (e.g., 10) and assemblies (e.g., 11) may be used in parallel to reduce the width of SI joint 62. For example, a first assembly (e.g., 11) can be inserted as described herein such that a first device (e.g., 10) extends across SI joint 62. Then, a second assembly (e.g., 11) can be inserted as described herein such that a second device (e.g., 10) extends across an SI joint 62 (i.e., at a location spaced from the first device). Each of the first and second devices (e.g., 10) can be alternatingly actuated as described herein in small increments to reduce the width of SI joint 62.

Some elements of the present devices (e.g., 10) may be configured in different sizes to accommodate a wide variety of patients. For example, a threaded portion (e.g., 46) of an inner anchor (e.g., 22) may be configured to include any appropriate longitudinal length, such as, for example, any one of, or between any two of: 10, 15, 20, 25, 30, 35, 40, 45, 50, 55, 60, 65, 70, 75, 80, 85, 90, 95, and 100 millimeters. For further example, a threaded portion (e.g., 102) of an outer anchor (e.g., 26) may be configured to include any appropriate longitudinal length such as, for example, any one of, or between any two of: 10, 12, 14, 16, 18, 20, 22, 24, 26, 28, 30, 32, 34, 36, 38, and 40 millimeters. In some embodiments, a sterile kit may include an assembly (e.g., 11) having one or more inner anchor(s) (e.g., 22) having a length as described herein and one or more outer anchor(s) (e.g., 26) having a length described herein.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and devices are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. An anchor device for use in sacroiliac joint stabilization, comprising:
 a housing having one or more apertures and defining a bore extending between a first and second end of the housing, wherein the housing includes:
  a first anchor defining the first end of the housing, wherein at least a portion of the first anchor includes a threaded outer surface, and
  a second anchor defining the second end of the housing, the second anchor being longitudinally movable relative to the first anchor, wherein at least a portion of the second anchor includes a threaded outer surface,
  wherein the threaded surface of the first anchor and the threaded surface of the second anchor are timed such that each of the threaded surfaces form a single thread groove in a cortical wall of an ilium and
  wherein the first anchor and the second anchor cooperate to define the one or more apertures;
 one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures;
 an actuating screw configured to mate with a threaded inner surface of the housing and be longitudinally movable in the bore of the housing, wherein the actuating screw is configured to effectuate movement of the at least one of the one or more engagement members between the retracted position and the extended position such that, when the at least one of the one or more engagement members is in the extended position;
  the at least one of the one or more engagement members is configured to be disposed within cancellous bone of a sacrum,
  the threaded outer surface of the first anchor is configured to contact a cortical wall of the sacrum, and
  the threaded outer surface of the second anchor is configured to contact a cortical wall of the ilium;
 a compression screw configured to mate with the threaded inner surface of the housing and be longitudinally movable in the bore of the housing, wherein the compression screw is rotatable relative to a longitudinal axis of the housing to cause the first anchor to move toward the second anchor along the longitudinal axis; and
 wherein the anchor device comprises a continuous channel extending from a first end of the anchor device to a second end of the anchor device, the channel being configured to receive a guidewire.

2. The device of claim 1, wherein the actuating screw is configured to engage and translationally move a carriage housing in order to effectuate movement of the at least one of the one or more engagement members between the retracted position and the extended position.

3. The device of claim 1, wherein the at least one of the one or more engagement members is rotatable between the retracted position and the extended position.

4. The device of claim 3, wherein the at least one of the one or more engagement members is rotatable toward a cortical wall of the sacrum.

5. The device of claim 1, wherein the at least one of the one or more engagement members comprises a contact surface configured to compress cancellous bone against an inner surface of a cortical wall of the sacrum when the engagement member is in the extended position.

6. The device of claim 5, wherein
 when the at least one of the one or more engagement members is in the extended position, the contact surface is spaced a distance from the threaded outer surface of the first anchor, the distance being at least greater than the largest depth of the threads of the threaded outer surface of the first anchor.

7. The device of claim 1, wherein the at least one of the one or more engagement members comprises a contact surface configured to contact an inner surface of a cortical wall of the sacrum when the engagement member is in the extended position.

8. The device of claim 1, wherein the one or more engagement members are longitudinally movable relative to the housing.

9. The device of claim 1, wherein the second end hag of the housing has a diameter at least 10 percent smaller than the housing's largest diameter.

10. An assembly for use in sacroiliac joint ("SI joint") stabilization, comprising:
 the device of claim 1; and
 a driver tool configured to thread the device across the SI joint.

11. The assembly of claim 10, wherein the driver tool includes a cannula coupled to a handle, the cannula and the handle each defining a channel configured to receive a guidewire.

12. The device of claim 1, wherein the threaded inner surface of the housing is defined by the first anchor.

13. The device of claim 1, wherein the housing includes a shoulder configured to engage the compression screw to restrict longitudinal movement of the compression screw relative to the housing.

14. The device of claim 13, wherein the compression screw is rotatable relative to the longitudinal axis of the housing to cause the first anchor to move toward the second anchor along the longitudinal axis while the compression screw is engaged with the shoulder of the housing.

15. A method of using an anchor device to stabilize a sacroiliac joint ("SI joint"), comprising
 inserting a guidewire across an SI joint such that the guidewire extends through an ilium and at least partially into a sacrum;
 positioning an anchor device over the guidewire, where the anchor device includes:
  a housing defining a bore extending between a first end and a second end of the housing, wherein the housing comprises:

an inner anchor defining the first end of the housing, wherein at least a portion of the inner anchor includes a threaded outer surface;

an outer anchor defining the second end of the housing, wherein at least a portion of the outer anchor includes a threaded outer surface and the threaded surface of the inner anchor and the threaded surface of the outer anchor are timed such that each of the threaded surfaces form a single thread groove in a cortical wall of the ilium; and one or more apertures defined by at least one of the inner anchor and the outer anchor;

one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures;

wherein the anchor device comprises a continuous channel extending from a first end of the anchor device to a second end of the anchor device, the channel being configured to receive the guidewire;

moving the anchor device across the SI joint such that the device extends through the ilium and at least partially into the sacrum whereby the threaded outer surface of the inner anchor contacts a cortical wall of the sacrum and the threaded outer surface of the outer anchor contacts a cortical wall of the ilium;

mating an actuating screw with a threaded inner surface of the housing and moving the actuating screw in the channel bore of the housing toward the second end of the housing;

longitudinally moving the at least one of the one or more engagement members toward the second end of the housing;

rotating the at least one of the one or more engagement members from the retracted position to the extended position, to cause the at least one of the one or more engagement members to extend into cancellous bone of the sacrum;

mating a compression screw with the threaded inner surface of the housing and moving the compression screw in the bore of the housing toward the second end of the housing;

engaging the compression screw with a shoulder of the housing;

rotating the compression screw relative to a longitudinal axis of the housing after the compression screw engages the shoulder of the housing; and urging, when the at least one of the one or more engagement members is in the extended position, the inner anchor towards the outer anchor to reduce a width of the SI joint;

wherein moving the actuating screw toward the second end of the housing causes:
the longitudinal movement of the at least one of the one or more engagement members toward the second end of the housing, and
the rotation of the at least one of the one or more engagement members from the retracted position to the extended position; and wherein rotating the compression screw after the compression screw engages the shoulder of the housing causes the inner anchor to be urged towards the outer anchor to reduce the width of the SI joint.

16. The method of claim 15, where, when the anchor device is positioned across the SI joint, the one or more engagement members are longitudinally spaced from the cortical wall of the sacrum by a distance such that the at least one of the one or more engagement members are movable to the extended position.

17. The method of claim 15, comprising positioning a tissue shield over the guidewire before positioning the anchor device over the guidewire.

18. The method of claim 15, comprising enlarging a space around the guidewire after the guidewire has been inserted across the SI joint.

19. The method of claim 15, comprising:
inserting a second guidewire across the SI joint such that the second guidewire extends through the ilium and at least partially into the sacrum;
positioning a second anchor device over the second guidewire, where the second anchor device includes:
a second housing defining a bore extending between a first end and a second end of the second housing, wherein the second housing comprises:
a second inner anchor defining the first end of the second housing, wherein at least a portion of the second inner anchor includes a threaded outer surface;
an second outer anchor defining the second end of the second housing, wherein at least a portion of the second outer anchor includes a threaded outer surface and the threaded surface of the second inner anchor and the threaded surface of the second outer anchor are timed such that each of the threaded surfaces form a single thread groove in a cortical wall of the ilium; and
one or more apertures defined by at least one of the second inner anchor and the second outer anchor;
one or more engagement members at least partially disposed in the second housing, where at least one of the one or more engagement members is movable between a retracted position and an extended position such that, when the at least one of the one or more engagement members is in the extended position, the at least one of the one or more engagement members extends through at least one of the one or more apertures;
wherein the second anchor device comprises a continuous channel extending from a first end of the second anchor device to a second end of the second anchor device, the channel being configured to receive the second guidewire;
moving the second anchor device across the SI joint such that the second anchor device extends through the ilium and at least partially into the sacrum whereby the threaded outer surface of the second inner anchor contacts a cortical wall of the sacrum and the threaded outer surface of the second outer anchor contacts a cortical wall of the ilium;
mating a second actuating screw with a threaded inner surface of the second housing and moving the second actuating screw in the bore of the second housing toward the second end of the second housing;
longitudinally moving the at least one of the one or more engagement members toward the second end of the second housing;
rotating the at least one of the one or more engagement members of the second anchor device from the retracted position to the extended position to cause the at least one of the one or more engagement members to extend into cancellous bone of the sacrum;

mating a second compression screw with the threaded inner surface of the second housing and moving the second compression screw in the bore of the second housing toward the second end of the second housing;

engaging the second compression screw with a shoulder of the second housing;

rotating the second compression screw relative to a longitudinal axis of the second housing after the second compression screw engages the shoulder of the second housing;

urging, when the at least one of the one or more engagement members of the second anchor device is in the extended position, the second inner anchor of the second anchor device towards the second outer anchor of the second anchor device to reduce a width of the SI joint;

wherein moving the second actuating screw toward the second end of the second housing causes:
  the longitudinal movement of the at least one of the one or more engagement members toward the second end of the second housing, and
  the rotation of the at least one of the one or more engagement members from the retracted position to the extended position; and wherein rotating the second compression screw after the second compression screw engages the shoulder of the second housing causes the second inner anchor to be urged towards the second outer anchor to reduce the width of the SI joint.

* * * * *

UNITED STATES PATENT AND TRADEMARK OFFICE
CERTIFICATE OF CORRECTION

PATENT NO. : 10,864,029 B2
APPLICATION NO. : 16/257789
DATED : December 15, 2020
INVENTOR(S) : Andy J. Redmond et al.

It is certified that error appears in the above-identified patent and that said Letters Patent is hereby corrected as shown below:

In the Claims

In Claim 9, Column 12, Line 35, delete "hag"

In Claim 15, Column 13, Line 35, delete "channel"

Signed and Sealed this
Nineteenth Day of December, 2023

Katherine Kelly Vidal
*Director of the United States Patent and Trademark Office*